US006093740A

United States Patent [19]
Jirousek et al.

[11] Patent Number: 6,093,740
[45] Date of Patent: Jul. 25, 2000

[54] THERAPEUTIC TREATMENT FOR SKIN DISORDERS

[75] Inventors: Michael Robert Jirousek; Lawrence E. Stramm; Louis Vignati; Douglas Kirk Ways, all of Indianapolis, Ind.

[73] Assignee: Eli Lilly and Company, Indianapolis, Ind.

[21] Appl. No.: 09/057,541

[22] Filed: Apr. 9, 1998

Related U.S. Application Data

[60] Provisional application No. 60/044,431, Apr. 30, 1997.

[51] Int. Cl.$^7$ .......................... A61K 31/40; A61K 31/405; C07D 209/04; C07D 403/14
[52] U.S. Cl. ........................... 514/414; 514/415; 548/491
[58] Field of Search ................................... 514/414, 415; 548/491

[56] References Cited

U.S. PATENT DOCUMENTS

| | | | |
|---|---|---|---|
| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 | 9/1996 | Heath, Jr. et al. | 514/183 |
| 5,621,098 | 4/1997 | Heath, Jr. et al. | 540/472 |
| 5,710,145 | 1/1998 | Engel et al. | 514/183 |

FOREIGN PATENT DOCUMENTS

0657411 A1   2/1994   European Pat. Off. .

OTHER PUBLICATIONS

Claffey, et al., *Cancer Research*, 56:172–181 (1996).
Denekamp J., *The British Journal Of Radiology*, 66(783):181–196 (1993).
Flier, et al., *The New England Journal Of Medicine*, 333(26): 1757–1763 (1995).
Folkman, J., "Tumor Angiogenesis", *The Molecular Basis of Cancer*, Mendelsohn, et al., Pub., W.B. Saunders Company, 206–232 (1995).
Muthukrishnan, et al., *Journal Of Cell Physiology*, 148:1–16 (1991).
Pepper, et al., *Biochemical And Biophysical Research Communications*, 189(2):824–831 (1992).
Aiello, et al., *The New England Journal Of Medicine*, 331(22):1480–1487 (1994).
Amin, et al., *Investigative Ophthalmology & Visual Science*, 35(8):3178–3188 (1994).
Bird, *Survey Of Ophthalmology*, 28 (Supplement):433–436 (1984).
Chan, et al., *Ophthalmology*, 101(2):289–300 (1994).
Cunha–Vaz, et al., *Survey Of Ophthalmology*, 28 (Supplement):485–492.
Freund, et al., *American Journal Of Ophthalmology*, 115:786–791 (1993).
Friedman, et al., *American Journal Of Kidney Diseases*, 26(1):202–208 (1995).
Jampol, et al., *Survey Of Ophthalmology*, 28 (Supplement):535–539 (1984).
Kirkpatrick, et al., *Br. J. Ophthalmol.*, 77:766–770 (1993).
Klein, et al., "Prevalence Of Age Related Maculopathy: The Beaver Dam Eye Study," *Ophthalmology*, 99(6):933–943 (1992).
Klein, et al., *Medical Clinics Of North American*, 72(6):1415–1437 (1988).
Liebowitz, et al., "The Framingham Eye Study: VI. Macular Degeneration," *Survey Of Ophthalmol.*, 24 (Supplement):428–457 (1980).
MPS Group, *Arch. Ophthalmol.*, 109:1232–1241 (1991).
Raskin, et al., *Annals Of Internal Medicine*, 117(3):226–233 (1992).
Yannuzzi, *Survey Of Ophthalmology*, 28:540–553 (1984).
Yannuzzi, et al., *Ophthalmology*, 88(9):947–554 (1981).
Van Effenterre, et al., *J. Fr. Ophthalmol.*, 16(11):602–610 (1993).
Jacobson et al., "Anti–inflammatory Properties of Go 6850: A Selective Inhibitor of Protein Kinase C," J. of Pharm. Expl. Ther., vol. 275, No. 2, pp. 995–1002, Nov. 1995.

*Primary Examiner*—Johann Richter
*Assistant Examiner*—Jane Oswecki
*Attorney, Agent, or Firm*—Paul R. Darkes

[57] ABSTRACT

A method for reducing or inhibiting vascular permeability especially the increased vascular permeability associated with VPF/VEGF, and dermal edema exhibited with bullous phemigoid, erythema multiforme, dermatitis herpetiformis, contact dermatitis/delayed hypersensitivity is disclosed, particularly using the β-isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione and its pharmaceutically acceptable salts.

10 Claims, No Drawings

THERAPEUTIC TREATMENT FOR SKIN DISORDERS

This application claims the benefit of copending provisional application Ser. No. 60/044,431, fled Apr. 30, 1997, which is incorporated by reference herein.

BACKGROUND OF THE INVENTION

1. Field of the Invention

The present invention is broadly directed to a method of inhibiting or decreasing vascular permeability associated with dermal edema, e.g., induration, and especially the increased vascular permeability induced by vascular permeability factor (VPF)/vascular endothelial growth factor (VEGF). The present invention is particularly directed to the use of Protein Kinase C (PKC) inhibitors, especially a particular class of isozyme selective PKC inhibitors for treating bullous phemigoid, erythema multiforme, dermatitis herpetiformis, contact dermatitis/delayed hypersensitivity, and allergic skin conditions.

2. Description of Related Art

Dermatological disorders such as bullous phemigoid, erythema multiforme, dermatitis herpetiformis, contact dermatitis, and allergic skin conditions are characterized by dermal edema. Bullous pemphigoid usually occurs in the elderly and may affect any of or all the skin and mucosal surfaces. Dermatitis herpetiformis is characterized by intensely pruritic, grouped vesicles which tend to be symmetrically distributed on the extensor surfaces of the limbs and over the scalp, buttocks, and back.

Erythema multiforme syndrome is a characteristic response of the skin and mucous membranes that is related to a number of possible etiologies, including infectious agents (herpesvirus hominis, *Mycoplasma pneumoniae*) and drugs (especially penicillin, antipyretics, barbiturates, hydantoins, and sulfonamides). In 50 percent of patients no etiology is ascertained. The major pathologic change in erythema multiforme is an acute lymphohistiocytic inflammatory infiltrate around blood vessels and may include degenerative changes in the endothelial cells of the capillaries and marked papillary dermal edema. The lesions occur in a characteristic symmetrical distribution and the syndrome may also include severe toxemia and prostration, high fever, cough, and "patchy" inflammation of the lungs.

Contact dermatitis/delayed hypersensitivity is a dermatological condition that is characterized by red indurated cutaneous lesions occurring hours to days after exposure to a sensitizing agent. Poison ivy is one of the common sensitizing agents to cause such skin condition.

These skin conditions are associated with vascular hyperpermeability and dermal edema (Macvicar D, et al, 1963; J Invest Dermatol 41:289; Pierard J and Whimster L 1961; Br J Dermatol 73:253). Hyperpermeability of the surrounding microvasculature is a constant feature of contact dermatitis/delayed hypersensitivity (Voisin et al, Ann. Inst. Pasteur. 104: 169, 1963). Recent studies have implicated VPF/VEGF in the formation of the dermal edema and subepidermal bullae formation (Brown L, et al, 1995; J Invest Dermatol 104:744). Recent investigations have demonstrated the presence of VPF/VEGF in monocytes/macrophages and keratinocytes in experimental models of contact dermatitis/delayed hypersensitivity reactions (Brown et al., J Immunol. 154: 2801, 1995). VEGF levels are significantly increased in skin lesions manifesting the disease entities described above. In particular, patients with the aforementioned skin lesions display extremely high levels of VEGF in the bullae of these lesions. Therapeutic treatments such as corticosteroids, and sulfone or sulfapyridine therapy have been developed over the years to treat these blistering disorders. However, there is still a need in the art to develop new therapeutic agents for skin lesion treatment, especially therapeutic agents targeted at the VPF/VEGF stimulated vascular permeability.

SUMMARY OF THE INVENTION

It is an object of the invention to provide methods for treating dermal edema.

It is another object of the invention to provide methods for inhibiting VPF/VEGF stimulated vascular permeability associated with dermal edema.

These and other objects of the invention are provided by one or more of the embodiments described below.

In one embodiment of the invention there is provided a method for treating dermal edema which comprises administrating to a mammal in need of such treatment a therapeutically effective amount of a protein kinase C inhibitor.

In another embodiment of the invention there is provided a method for reducing or inhibiting VPF/VEGF stimulated vascular permeability associated with dermal edema which comprises administrating to a mammal in need of such treatment a therapeutically effective amount of a protein kinase C inhibitor.

The present invention provides the art with a method for treating, such as reducing or inhibiting, vascular permeability associated with dermal edema such as induced by VPF/VEGF. The method is effective in treating bullous phemigoid, erythema multiforme, dermatitis herpetiformis, contact dermatitis/delayed hypersensitivity, and allergic skin conditions.

DETAILED DESCRIPTION OF THE INVENTION

It is a discovery of the present invention that use of PKC inhibitors, especially a particular class of protein kinase C inhibitors, reduces or inhibits vascular permeability associated with dermal edema, especially the increased vascular permeability induced by VPF/VEGF. Consequently, such compounds can be used therapeutically to treat skin conditions associated with dermal edema, e.g., bullous phemigoid, erythema multiforme, dermatitis herpetiformis, contact dermatitis/delayed hypersensitivity, and allergic skin conditions.

The method of this invention preferably utilizes those protein kinase C inhibitors that effectively inhibit the $\beta$ isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylnaleimides are particularly represented by the compounds of formula I. These compounds, and methods for their preparation, have been disclosed in U.S. Pat. No. 5,552,396, which is incorporated herein by reference. These compounds are administered in a therapeutically effective amount (such as a VPF/VEGF inhibiting amount) to a mammal to reduce or inhibit vascular permeability, especially to reduce or inhibit VPF/VEGF stimulated vascular permeability. In particular, these compounds can be used to treat dermal edema associated with vascular permeability, e.g., bullous phemigoid, erythema multiforme, dermatitis herpetiformis, contact dermatitis/ delayed hypersensitivity, and allergic skin conditions.

One preferred class of compounds for use in the method of the invention has the formula:

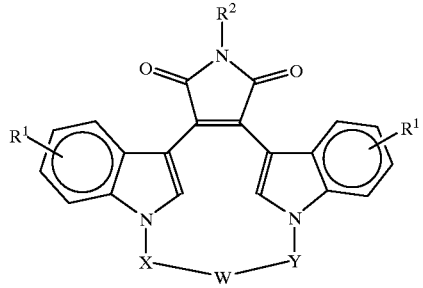

(I)

wherein:

W is —O—, —S—, —SO—, —SO$_2$—, —CO—, C$_2$–C$_6$ alkylene, substituted alkylene, C$_2$–C$_6$ alkenylene, —aryl—, —aryl(CH$_2$)$_m$O—, —heterocycle—, —heterocycle—(CH$_2$)$_m$O—, —fused bicyclic—, —fused bicyclc—(CH$_2$)$_m$O—, —NR$^3$—, —NOR$^3$—, —CONH—, or —NHCO—;

X and Y are independently C$_1$–C$_4$ alkylene, substituted allylene, or together X Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted allylene, —O—, S—, —CONH—, —NHCO— or —NR$^3$—. Particularly preferred compounds for use in the invention are compounds of the formula Ia:

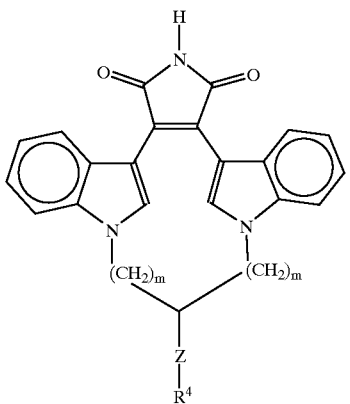

(Ia)

wherein Z is —(CH$_2$)$_p$— or —(CH$_2$)$_p$—O—(CH$_2$)$_p$—; R$^4$ is hydroxy, —SH, C$_1$–C$_4$ alyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ ally; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$.

Other preferred compounds for use in the method of the present invention are compounds wherein W in formula I is —O—, Y is a substituted alkylene, and X is an allylene. These preferred compounds are represented by formula Ib:

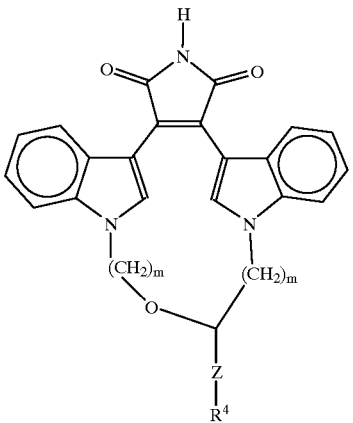

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used. Mesylate salts are disclosed in U.S. Pat. No. 5,710,145 (incorporated herein by reference).

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase C inhibitor for use in the method of this invention is the compound described in Example 5g ((S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts.

A preferred mesylate salt can be prepared by reacting a compound of the formula II

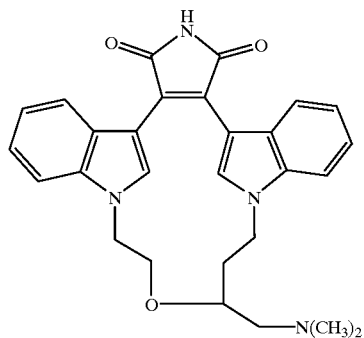

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art directly from the reaction mixture in yields ranging from 50% to 100%. Recrystallization and other purification techniques known in the art may be used to purify the salt further if desired.

Applicants believe that VPF/VEGF elicits increased vascular permeability associated with dermal edema via activation of PKC, especially PKC-β. PKC-β is also needed for antigen presentation by monocytes in response to sensitizing agents. Therefore, PKC inhibitors, particularly PKC-β inhibitors can be used to attenuate or inhibit dermal edema, especially dermal edema associated with enhanced cellular and/or vascular permeability stimulated or induced by VPF/VEGF.

The compounds identified by the present invention can be used to treat the clinical manifestations of various skin conditions associated with dermal edema. Dermal edema is characterized by an accumulation of fluid extractive from vascular space into dermal interstitial space which could form blister formation. Blister formations generally are exhibited in two major forms: vesicles and bullae which are circumscribed elevated lesions containing fluid.

Dermal edema is the major feature of a number of skin disorders: certain bacterial and viral infections; allergic skin conditions, e.g., angioneurotic edema and atopic dermatitis; trauma from mechanical, thermal, or chemical agents; and most important, the bullous diseases of unknown causes such as pemphigus. In particular, dermal edema is a major symptom found in bullous phemigoid, erythema multiforme, dermatitis herpetiformis, contact dermatitis/delayed hypersensitivity, and allergic skin conditions induced by various sensitizing agents. All of the skin disorders described above can be treated with the compounds of the present invention.

One skilled in the art will recognize that a therapeutically effective amount (such as a VPF/VEGF inhibiting amount) of the protein kinase C inhibitor of the present invention is the amount sufficient to inhibit vascular permeability, VPF/VEGF activity associated with vascular permeability, or dermal edema, and that this amount varies inter alia, depending upon the size and the type of skin lesions, the concentration of the compound in the therapeutic formulation, and the condition of the patient. Both in vivo and in vitro tests can be used to determine an amount of a compound needed for inhibiting vascular permeability and dermal edema. For example, upon administering a compound provided by the present invention, vascular permeability can be measured by fluorescein, trypan blue leakage out of the vascular system and into the skin, or any means known in the art; dermal edema can be readily detected by clinical examinations, well within the ability of a skilled artisan. A rodent model of contact dermatitis (Brown et al., *J. Immunol* 154: 2801, 1995) can be used to evaluate the effectiveness of the compounds of the present invention. Urushiol, the extract from poison ivy could also be used in human for testing the effectiveness of the compounds by measuring the size of dermal edema, e.g., induration of the lesion. Generally, an amount of protein kinase C inhibitor to be administered as a therapeutic agent for treating skin lesions associated with dermal edema will be determined on a case by case basis by the attending physician. As a guideline, the extent of the lesion, the body weight and age of the patient will be considered when setting an appropriate dose.

Generally, a suitable dose is one that results in a concentration of the protein kinase C inhibitor at the treatment site in the range of 0.5 nM to 200 $\mu$M, and more usually 20 nM to 80 nM. It is expected that serum concentrations of 20 nM to 80 nM should be sufficient in most circumstances.

To obtain these treatment concentrations, a patient in need of treatment likely will be administered between about 0.1 mg per day per kg of body weight and 1.5 mg per day per kg. Usually, not more than about 1.0 mg per day per kg of body weight of protein kinase C inhibitor should be needed. As noted above, the above amounts may vary on a case-by-case basis.

The present invention also contemplates the prophylatic use of the compounds disclosed herein to prevent or inhibit the severity of such skin disorder. It is contemplated that suitable prophylatic dosages will typically be at the lower end of the range required for treating an active disorder.

The compounds of formula I, and the preferred compounds of formulae Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 64 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be, and most often will be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfite; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon an affected tissue size and concentration of compound in the formulation Generally, the formulation will be applied to the effected tissue in an amount affording from about 1 to about 500 µg compound per cm² of an affected tissue. Preferably, the applied amount of compound will range from about 30 to about 300 µg/cm², more preferably, from about 50 to about 200 µg/cm², and, most preferably, from about 60 to about 100 µg/cm².

The following formulation examples are illustrative only and are not intended to limit the scope of the invention in any way.

Formulation 1

Hard gelatin capsules are prepared using the following ingredients:

|  | Quantity (mg/capsule) |
|---|---|
| Active agent | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
|---|---|
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

Tablets each containing 60 mg of active ingredient are made as follows:

|  | Quantity (mg/tablet) |
|---|---|
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method for treating a dermatological disorder characterized by dermal edema by reducing VPF/VEGF stimulated vascular permeability, comprising the step of:

administering a therapeutically effective amount of a β isozyme selective protein kinase C inhibitor to a mammal in need of such treatment, wherein the dermatological disorder is selected from the group consisting of bullous phemigoid, erythema multiforme, dermatitis herpetiformis, contact dermatitis/delayed hypersensitivity, dermatological disorders associated with bacterial or viral infections, trauma from mechanical or thermal agents, and allergic skin conditions.

2. The method of claim 1 wherein the protein kinase C inhibitor has the following formula:

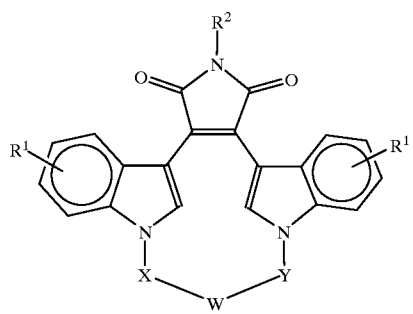

(I)

wherein:
- W is —O—, —S—, —S—, —SO$_2$—, —CO—, C$_2$-C$_6$ alkylene, substituted alkylene, C$_2$-C$_6$ alkenylene, —aryl—, —aryl(CH$_2$)$_m$O—, —heterocycle—, —heterocycle—(CH$_2$)$_m$O—, —fused bicyclic—, —fused bicyclic—(CH$_2$)$_m$O—, —NR$^3$—, —NOR$^3$—, —CONH—, or —NHCO—;
- X and Y are independently C$_1$-C$_4$ alkylene, substituted allylene, or together X, Y, and W combine to form —(CH$_2$)$_n$—AA—;
- R$^1$'s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);
- R$^2$ is hydrogen, CH$_3$CO—, NH$_2$, or hydroxy;
- R$^3$ is hydrogen, (CH$_2$)$_n$aryl, C$_1$-C$_4$ alkyl, —COO(C$_1$-C$_4$ alkyl), —CONR$^4$R$^5$, —(C=NH)NH$_2$, —SO(C$_1$-C$_4$ alkyl), —SO$_2$ (NR$^4$R$^5$), or —SO$_2$ (C$_1$-C$_4$ alkyl);
- R$^4$ and R$^5$ are independently hydrogen, C$_1$-C$_4$ alkyl, phenyl, benzyl, or combine to the nitrogen to which they are bonded to form a saturated or unsaturated 5 or 6 member ring,
- AA is an amino acid residue;
- m is independently 0, 1, 2, or 3; and
- n is independently 2, 3, 4, or 5, or an acid salt thereof.

3. The method of claim 2 wherein the protein kinase C inhibitor has the following formula:

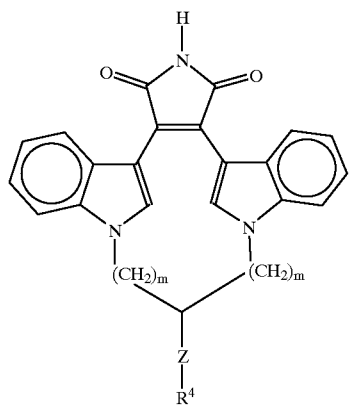

(Ia)

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$-C$_4$ alkyl; R$^6$ is hydrogen, C$_1$-C$_4$ alkyl or benzyl; p is 0, 1, or 2; and m is independently 2 or 3, or an acid salt thereof.

4. The method of claim 2 wherein the protein kinase C inhibitor has the following formula:

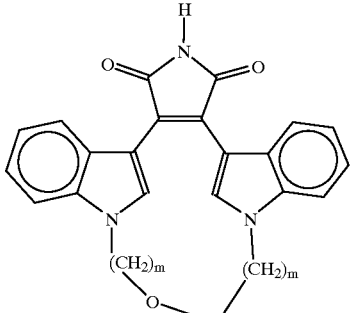

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$-C$_4$ alkyl; p is 0, 1, or 2; and m is independently 2 or 3, or an acid salt thereof.

5. The method of claim 2 wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1H)-pyrrole-2,5-dione or its acid salt.

6. A method for treating a blister formation by reducing VPF/VEGF stimulated vascular permeability, comprising the step of:
   administering to a mammal in need of such treatment of therapeutically effective amount of a β isozyme-selective protein kinase C inhibitor.

7. The method of claim 6 wherein the protein kinase C inhibitor has a formula:

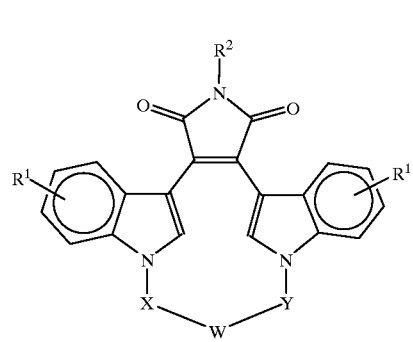

(I)

wherein:
- W is —O—, —S—, —SO—, —SO$_2$—, —CO—, C$_2$-C$_6$ alkylene, substituted alkylene, C$_2$-C$_6$ alkenylene, —aryl—, —aryl(CH$_2$)$_m$O—, —heterocycle—, —heterocycle—(CH$_2$)$_m$O—, —fused bicyclic—, —fused bicyclic—(CH$_2$)$_m$O—, —NR$^3$—, —NOR$^3$—, —CONH—, or —NHCO—;
- X and Y are independently C$_1$-C$_4$ alkylene, substituted alkylene, or together X, Y, and W combine to form —(CH$_2$)$_n$—AA—;
- R$^1$'s are hydrogen or up to four optional substituents independently selected from halo, C$_1$-C$_4$ alkyl, hydroxy, C$_1$-C$_4$ alkoxy, haloalkyl nitro, NR$^4$R$^5$, or —NHCO(C$_1$-C$_4$alkyl);

$R^2$ is hydrogen, $CH_3CO$—, $NH_2$, or hydroxy;

$R^3$ is hydrogen, $(CH_2)_n$aryl, $C_1$–$C_4$ alkyl, —COO($C_1$–$C_4$ alkyl), —CONR$^4$R$^5$, —(C=NH)NH$_2$, —SO($C_1$–$C_4$ alkyl), —SO$_2$ (NR$^4$R$^5$), or —SO$_2$($C_1$–$C_4$ alkyl);

$R^4$ and $R^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5, or an acid salt thereof.

8. The method of claim 6, wherein the protein kinase C inhibitor has a formula:

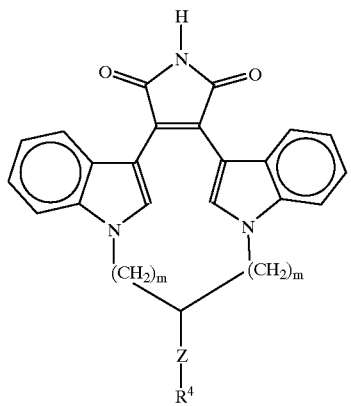

(Ia)

wherein Z is —(CH$_2$)$_p$— or —(CH$_2$)$_p$—O—(CH$_2$)$_p$—; $R^4$ is hydroxy, —SH, $C_1$–$C_4$ alkyl, (CH$_2$)$_m$aryl, —NH(aryl), —N(CH$_3$)(CF$_3$), —NH(CF$_3$), or —NR$^5$R$^6$; $R^5$ is hydrogen or $C_1$–$C_4$ alkyl; $R^6$ is hydrogen, $C_1$–$C_4$ alkyl or benzyl; p is 0, 1, or 2; and m is independently 2 or 3, or an acid salt thereof.

9. The method of claim 6 wherein the protein kinase C inhibitor has the following formula:

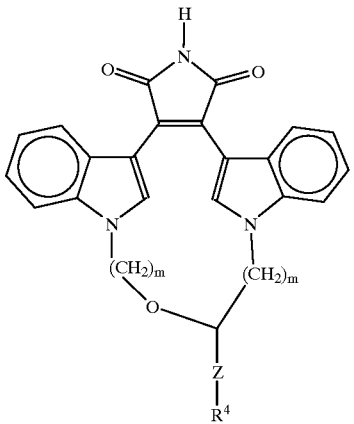

(Ib)

wherein Z is —(CH$_2$)$_p$—; $R^4$ is —NR$^5$R$^6$, —NH(CF$_3$), or —N(CH$_3$)(CF$_3$); $R^5$ and $R^6$ are independently H or $C_1$–$C_4$ alkyl; p is 0, 1, or 2; and m is independently 2 or 3, or an acid salt thereof.

10. The method of claim 6 wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its acid salt.

* * * * *

UNITED STATES PATENT AND TRADEMARK OFFICE
CERTIFICATE OF CORRECTION

PATENT NO.: 6,093,740
DATED: July 25, 2000
INVENTOR(S): Michael Robert JIROUSEK, et al.

It is certified that these errors appear in the above-identified patent and that said Letters Patent is hereby corrected as shown below:

In Claim 2, column 11, line 17:

"-S-" has been replaced with --SO--.

column 11, line 24:

"allylene" has been replaced with --alkylene--.

column 11, line 37:

"ring," has been replaced with --ring;--.

In Claim 5, column 12, line 28:

"-1H)-" has been replaced with -- -1(H)- --.

UNITED STATES PATENT AND TRADEMARK OFFICE
CERTIFICATE OF CORRECTION

PATENT NO. : 6,093,740
DATED : July 25, 2000
INVENTOR(S) : Michael Robert JIROUSEK, et al.

It is certified that error appears in the above-identified patent and that said Letters Patent is hereby corrected as shown below:

column 12, line 66:

"haloalkyl nitro" has been replaced with --haloalkyl, nitro--.

Signed and Sealed this

Seventeenth Day of April, 2001

Attest:

NICHOLAS P. GODICI

Attesting Officer          Acting Director of the United States Patent and Trademark Office